United States Patent [19]

Fischell et al.

[11] Patent Number: 5,011,490
[45] Date of Patent: Apr. 30, 1991

[54] ENDOLUMINAL TISSUE EXCISION CATHETER SYSTEM AND METHOD

[75] Inventors: Robert E. Fischell, Dayton, Md.; Tim A. Fischell, Los Altos, Calif.

[73] Assignee: Medical Innovative Technologies R&D Limited Partnership, Dayton, Md.

[21] Appl. No.: 447,187

[22] Filed: Dec. 7, 1989

[51] Int. Cl.$^5$ .............................................. A61B 7/22
[52] U.S. Cl. ................................... 606/159; 604/22; 128/751
[58] Field of Search ............... 606/159, 169, 170, 179; 604/22, 108, 264, 267; 128/751, 754, 755

[56] References Cited

U.S. PATENT DOCUMENTS

| | | | |
|---|---|---|---|
| 1,167,014 | 1/1916 | O'Brien | 606/159 |
| 2,505,358 | 4/1950 | Gusberg | 128/2 |
| 4,696,667 | 9/1987 | Masch | 604/22 |
| 4,732,154 | 3/1988 | Shiber | 606/159 |
| 4,765,332 | 8/1988 | Fischell et al. | 606/159 |
| 4,867,156 | 8/1989 | Stack et al. | 606/159 |
| 4,886,061 | 12/1989 | Fischell et al. | 128/305 |
| 4,898,575 | 2/1990 | Fischell et al. | 604/22 |

FOREIGN PATENT DOCUMENTS 2044103 10/1980 United Kingdom .

Primary Examiner—C. Fred Rosenbaum
Assistant Examiner—William W. Lewis

[57] ABSTRACT

An Endoluminal Tissue Excision Catheter (ETEC) is described which is capable of excising obstructive tissue from a vessel in a living body. The ETEC system operates by first passing a guide wire through the vessel and beyond the obstructive tissue. The ETEC catheter is then advanced over the guide wire until its distal end lies beyond the obstructive tissue. A closing catheter portion of ETEC is then pulled back from a cut/collect catheter portion of the ETEC thus exposing a cutting edge located at the proximal end of a cylindrical cutting blade located at a distal portion of the cut/collect catheter. A rotating means is then attached to the cut/collect catheters'3 s proximal end. The cut/collect catheter is then pulled back in a retrograde direction while rotating, thus cutting and collecting the excised obstructive tissue into a tissue collection chamber that is formed within the cylindrical cutting blade. The entire ETEC system including the cut/collect and closing catheters and the guide wire is then removed from the vessel. Means are provided to flush the collected tissue out of the tissue collection chamber after the ETEC catheter is outside of the living body.

29 Claims, 4 Drawing Sheets

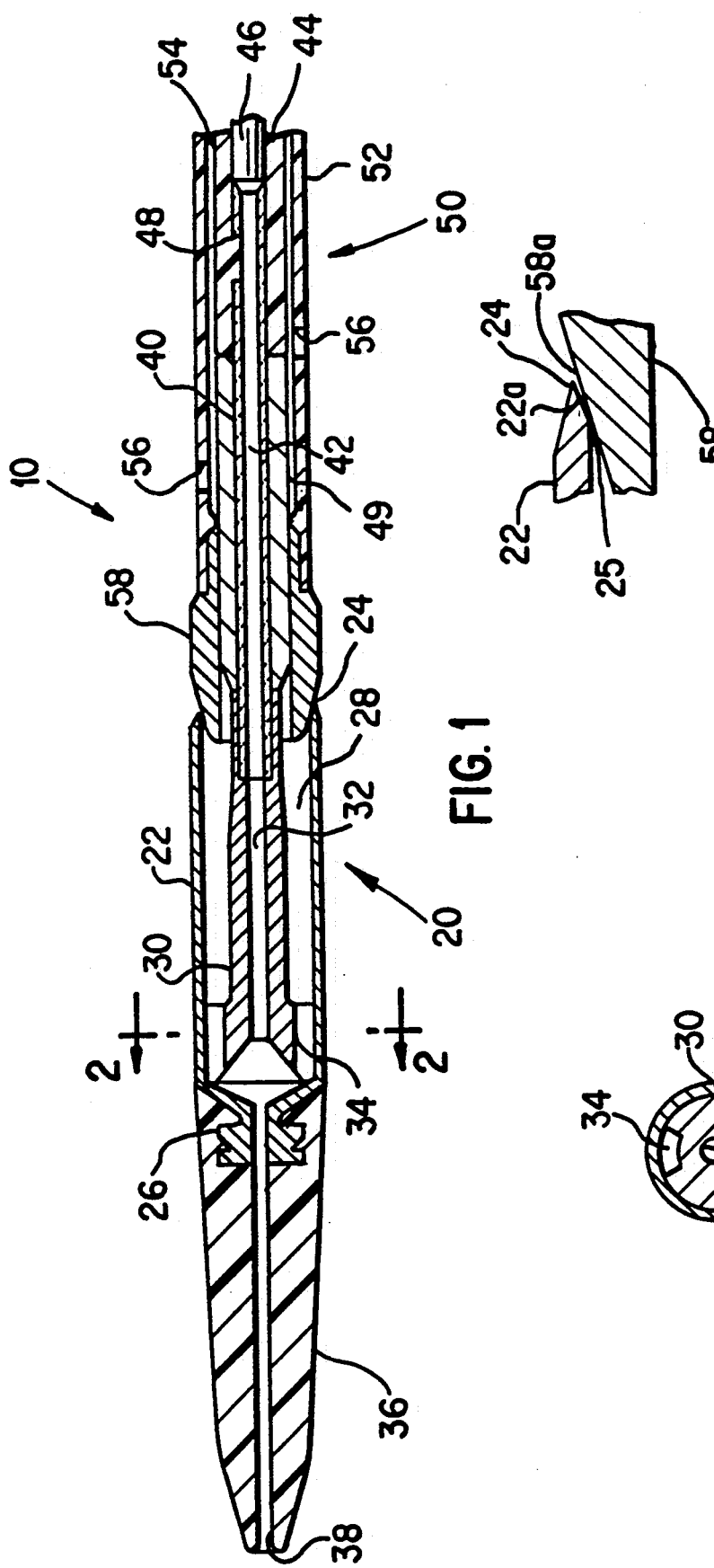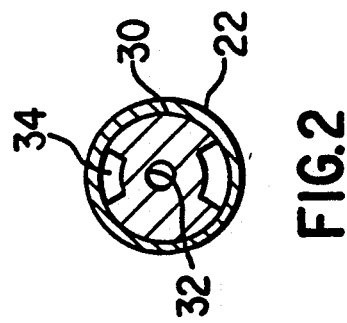

5,011,490

ENDOLUMINAL TISSUE EXCISION CATHETER SYSTEM AND METHOD

BACKGROUND OF THE INVENTION

1. Field of the Invention

This invention constitutes a means and method for the excision of tissue from within the lumen of a vessel in a human or animal by the use of an Endoluminal Tissue Excision Catheter (ETEC) system. Although much of the description herein concerns atherectomy of plaque from within an artery, this invention is more generally applicable to the excision of any tissue from any vessel of a living body.

2. Description of the Prior Art

There are numerous treatments to remove tissue from lumens within the vessels in a living body including surgical interventions such as endarterectomy and by-pass surgery using veins or artificial graft materials. Balloon angioplasty is becoming increasingly popular for the dilation of arterial stenoses without the excision of the plaque. More recently atherectomy, the excision from an artery of atheromatous plaque, has been successfully used to open arterial stenoses.

In UK Patent Application 2,044,103A by D.N. Ross dated Oct. 15, 1980 there is described a device for removing plaque within an artery by drawing together two cutting edges that are initially placed on either side of an arterial stenosis. There are numerous disadvantages of the Ross invention, namely: (1) two cutting edges are required which is more costly and complex as compared to one cutting edge, and two edges require very precise alignment in order to properly cut without tearing, (2) Ross does not teach a means to prevent dulling of the head's cutting edge 4 as it is pulled into the body 1, (3) no guide wire means is taught by Ross to guide the cutting head to and through the stenosis, (4) the entire distal portion is rigid for a considerable length; explicitly Ross lacks a long flexible tip thereby making it difficult for the catheter tip to pass through highly curved blood vessels, (5) Ross does not teach a means for injecting contrast media, (6) Ross does not teach a means for flushing out the excised tissue from the tissue collection chamber, and (7) Ross does not teach rotation or mechanical vibration of the cutting edge so as to enhance the cutting action.

U.S. Pat. No. 4,765,332, issued Aug. 23, 1988 to Robert E. and Tim A. Fischell, entitled "Pullback Atherectomy Catheter System," teaches a retrograde cutting catheter that can be advanced over a guide wire with a single cutting edge that can be rotated or mechanically vibrated, but does not teach a separate means to enclose the cut plaque in the plaque collection chamber after it has been cut or a means for injecting contrast media through the catheter's distal end, or several other novel and useful features of the invention described herein.

SUMMARY OF THE INVENTION

The Endoluminal Tissue Excision Catheter (ETEC) system as described herein is designed to overcome many of the shortcomings of the prior art devices. The Pullback Atherectomy Catheter (PAC), as described in U.S. Pat. No. 4,765,332 (which is incorporated herein by reference) also cuts in the retrograde direction, but does not have many of the unique and novel features of the ETEC system. ETEC has a flexible plastic tip which facilitates entry over a guide wire into the lumen of a vessel such as an artery. While it is being pushed forward through an arterial stenosis (or any obstructive tissue) the ETEC would be closed, i.e. the single cutting edge of the cut/collect catheter portion of the ETEC system would be in contact with a metal tip at the distal end of a closing catheter that surrounds most of the length of the cut/collect catheter. After ETEC's distal end is passed beyond the tissue to be excised, the closing catheter would then be pulled back so as to expose the single cutting blade. The cutting blade would then be pulled back (typically while rotating) and the excised tissue would collect into a tissue collection chamber until the blade was in contact with the metal tip at the distal end of the closing catheter. Thus the cut tissue would be completely contained.

The entire ETEC system would then be withdrawn from the vessel, and the excised tissue would be flushed from the tissue collection chamber. ETECs of sequentially larger diameter would be used until the largest catheter diameter that is used is just slightly smaller than the unoccluded luminal diameter of the vessel from which the tissue is being excised. At any time when the catheter is in the vessel, contrast media can be injected from the closing catheter's distal end, and fluoroscopy can then be used to define the state of the vessel.

When the cutting edge is in contact with the metal tip of the closing catheter, a unique geometry prevents dulling of the cutting edge.

Thus an object of the present invention is to excise tissue blocking a vessel in a living body by pulling back on a single cutting blade that may be rotating or mechanically oscillating while it cuts.

Another object of the present invention is for the cutting edge to close against the distal metal tip of a separate closing catheter so as to fully enclose the cut tissue.

Still another object of the present invention is to accomplish the closure without dulling the cutting edge.

Still another object of the present invention is to provide a means for having the ETEC follow a guide wire that has been advanced through the occlusive tissue.

Still another object of the present invention is to have a flexible tip means which enhances the ETEC's ability to follow a guide wire through significantly curved vessels.

Still another object of the present invention is to provide a short section of controlled length between the cutting edge and the distal metal tip of the closing catheter in which the vessel to have tissue excised is straightened so as to avoid perforation of the vessel wall while cutting.

Still another object of the present invention is to provide a method for cutting long lengths of occlusive tissue by keeping a controlled length of separation between the cutting edge and the distal metal tip while pulling the entire ETEC system back in a retrograde direction and then closing the cutting edge against the metal tip to seal the cut tissue within.

Still another object of the present invention is to provide a means for injecting contrast medium from holes near the distal end of the closing catheter.

Still another object of the present invention is to provide a novel means for flushing the cut tissue out of the tissue collection chamber after the ETEC has been removed from the living body.

Still another object of the present invention is to provide a separate rotational means which connects to the cut/collect catheter which has the capability of changing its audible tone when a greater resistance torque is experienced by the cutting edge.

Still another object of the present invention is to provide a rotator which can prevent the guide wire that passes through it from rotating when the cut/collect catheter is rotated.

Still another object of the present invention is to use the ETEC to perform endoluminal biopsy of tissue within a variety of vessels within a living body.

BRIEF DESCRIPTION OF THE DRAWINGS

FIG. 1 is a cross section of the distal end of the ETEC in a closed position.

FIG. 1a is an enlarged cross section showing how the distal end of the closing catheter makes contact with the cutting cylinder of the cut/collect catheter.

FIG. 2 is a transverse cross section of the ETEC at position 2—2 of FIG. 1.

DETAILED DESCRIPTION OF THE DRAWINGS

Figure 3:
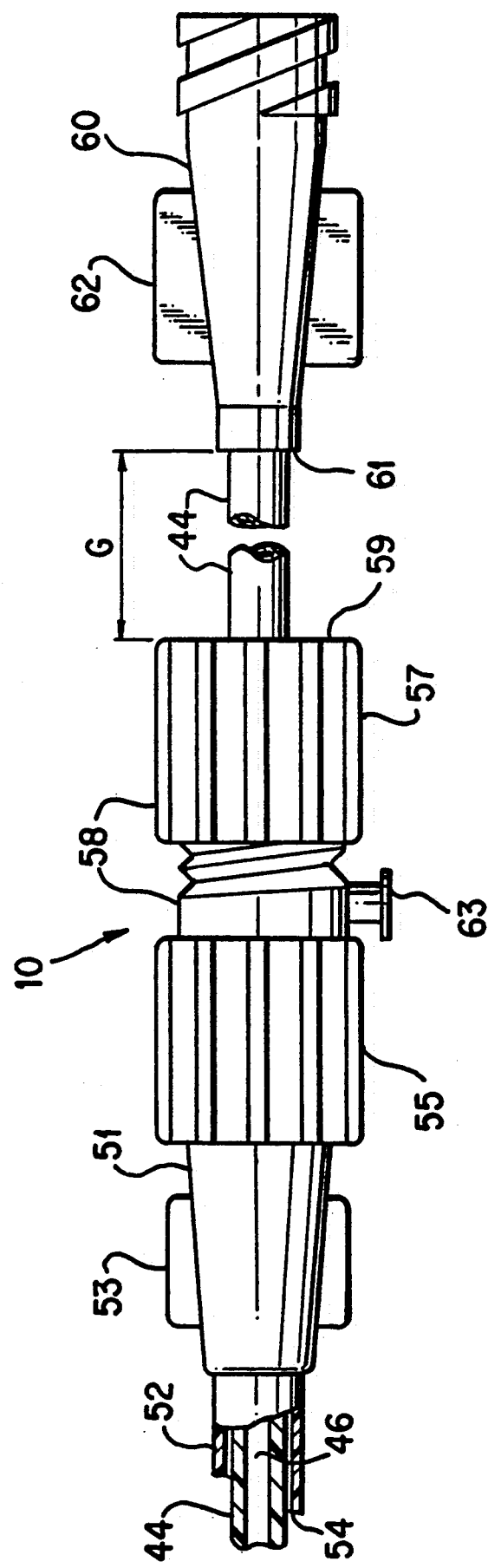
FIG. 3 is a partial section of the proximal end of the ETEC system.

FIG. 1 is a longitudinal cross-sectional view of the distal end of the ETEC system 10 which consists of a cut/collect catheter 20 and a closing catheter 50. The cut/collect catheter 20 has a cutting cylinder 22 with a cutting edge 24 at its proximal end and which cylinder 22 encloses a tissue collection chamber 28 where the cut tissue is collected. Inside the chamber 28 is a cylinder support 30 that (as also seen in FIG. 2 which is the section at 2—2 of FIG. 1) has two passageways 34 that allow fluid communication between the interior lumen 32 of the support 30 and the collection chamber 28. The support 30 would typically be spot welded at one or more points to the cylinder 22.

The cutting cylinder's distal end 26 is formed with indentations to securely hold onto a flexible plastic tip 36 which has a lumen 38 that is in fluid communication with the lumen 32.

The proximal end of the cylinder support 30 is welded to the distal end of a metal cannula 40 which has an interior lumen 42 as shown in FIG. 1. The proximal end of the cannula 40 is attached to the distal end of a plastic torqueing cylinder 44 which has a central lumen 46 which is in fluid communication with the other interior lumens of the ETEC 10. A machined cut-out 48 in the cannula 40 provides a secure mechanical attachment of the torqueing cylinder 44 to the cannula 40. A separate non-spinning washer cylinder 49 surrounds the metal cannula. Its function is to remain stationary relative to the tissue being excised while the cutting cylinder 22 is being rotated.

The distal end of the closing catheter 50 is also shown in FIG. 1. The closing catheter cylinder 52 surrounds the torqueing cylinder 44 of the cut/collect catheter.

A passageway 54 is formed between the outer surface of the torqueing cylinder 44 and the inner surface of the closing catheter cylinder 52. Solutions such as contrast media or medication can be injected at the proximal end of the closing catheter 50 (see FIG. 3) and that liquid will then enter an artery or other body vessel through one or more vent holes 56 at the distal end of the closing catheter 50. A metal tip 58 connected to the distal end of the cylinder 52 makes contact with the cutting cylinder 22 along a circle 25 as seen in the enlarged section in FIG. 1a. This construction (as can be seen, FIG. 1a shows the frustrum of a cone 58a which is the outer surface of the tapered distal portion of the metal tip 58 which has a smaller apex angle as compared to the apex angle of the frustrum of the cone 22a on the inner surface at the proximal end of the cutting cylinder 22. This construction prevents the edge 24 from coming in contact with the metal tip 58. Thus the edge 24 is not made dull by contacting the metal tip 58. This assures that the tissue collection chamber 28 can be closed off thus securing the excised tissue within, yet, the device can be used repeatedly without dulling the cutting edge 24. An alternative design (not shown) would be to have a plastic end for the cylinder 52 into which the edge 24 could be imbedded without becoming dull.

FIG. 2, a transverse cross section at position 2—2 of FIG. 1, shows the details of the two fluid passageways 34, the lumen 32 and the connection of the support 30 to the cutting cylinder 22.

FIG. 3 is a partial cross section of the proximal end of the ETEC system 10. To the left in FIG. 3 is shown a cross section of the torqueing catheter 44 having an interior lumen 46 and the closing catheter cylinder 52. A plastic Luer fitting 51 is molded onto the proximal end of the catheter 52. The two finger wings 53 are available to prevent rotation of the fitting 51 when the nut 55 is tightened. The nut 55 and sealing gland 57 are part of a Touhy-Borst fitting 58 which is used to seal off the proximal end of the passageway 54. A side-port 63 in the Touhy-Borst fitting 58 allows a syringe (not shown) to be connected for distally injecting contrast media through the distal vent hole(s) 56. Either a check valve or a single-port or a multiple-port stop cock can be connected at the side-port 63 to seal off the back flow of blood when the distal end of the ETEC 10 is placed in an artery. The sealing gland 57 in the Touhy-Borst fitting 58 seals against the outer surface of the torqueing cylinder 44. A Luer fitting 60 with two finger wings 62 is molded onto the proximal end of the torqueing cylinder 44. Since there is a passageway through the center of the entire ETEC 10, a guide wire can be inserted through the proximal end of the fitting 60 and then can be advanced until the distal end of the guide wire passes through the flexible tip 36 (see FIG. 1). Thus, a guide wire (as shown partially in FIG. 5) can first be advanced within the lumen of a human (or animal) vessel and the entire ETEC system 10 can then be advanced over the guide wire to that site in the vessel where tissue is to be excised.

As seen in FIG. 3 the proximal end of the ETEC 10 is designed so that there is a gap G between the proximal surface 59 of the Touhy-Borst fitting 58 and the distal surface 61 of the Luer fitting 60. This gap G determines the maximum distance that the cutting edge 24 of the cut/collect catheter 20 (see FIG. 5) can be separated from the metal tip 58 of the closing catheter 50. This gap G would typically be between 1 and 30 mm long.

Figure 4:
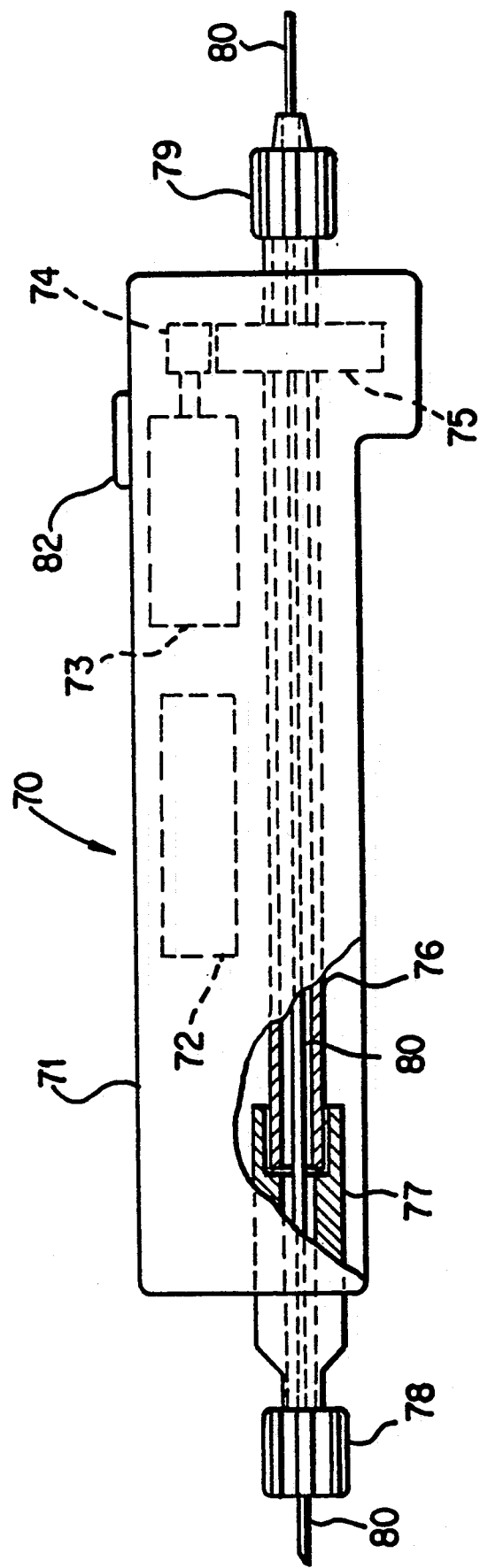
FIG. 4 shows a partial section of the rotator which is used to spin the cut/collect catheter portion of the ETEC system.

FIG. 4 shows a rotator 70 which has a case 71 which encloses a battery 72 and a d-c motor-gear reducer assembly 73. When the switch 82 on top of the case 71 is pressed, the battery is electrically connected to the motor assembly 73 which causes rotation of the motor shaft onto which is mounted the small spur gear 74 which in turn rotates the large spur gear 75 which is mechanically joined to the rotating tube 76. The rotating tube 76 is attached at its distal end to a Luer fitting 79 which can be securely connected to the Luer fitting 60 (FIG. 3) located at the proximal end of the cut/collect catheter 20. When connected, these fittings provide a mechanical connection which is also a fluid seal.

At its proximal end, rotating tube 76 nests into a rear cylinder 77 which does not rotate. The proximal end of the cylinder 77 has a sealing gland 78 that seals against the guide wire 80 to prevent the distal tip of the guide wire 80 from whipping around in the vessel when the cut/collect catheter 20 is being rotated. As can be seen in FIG. 4, the guide wire passes through the entire length of the rotator 70 as well as extending through the entire length of the ETEC 10.

The torque vs rotational speed curve of the rotator is such that at essentially zero torque, the rotating cylinder 76 (and therefore the cut/collect catheter 20) would rotate at approximately 2000 RPM. When the cutting edge 24 encounters a resistive torque, as would be experienced when it cuts through highly calcified plaque or when the edge 24 engages the metal tip 58, the rotation rate slows considerably. The slower rotation rate is detected by the ETEC operator as a decreased audible tone which indicates that the cut is completed or that there is more resistive torque being experienced by the cutting edge 24. This feature of a detectable audible tone which depends upon the resistive torque provides valuable information to the operator when performing tissue excision from a vessel.

Figure 5:
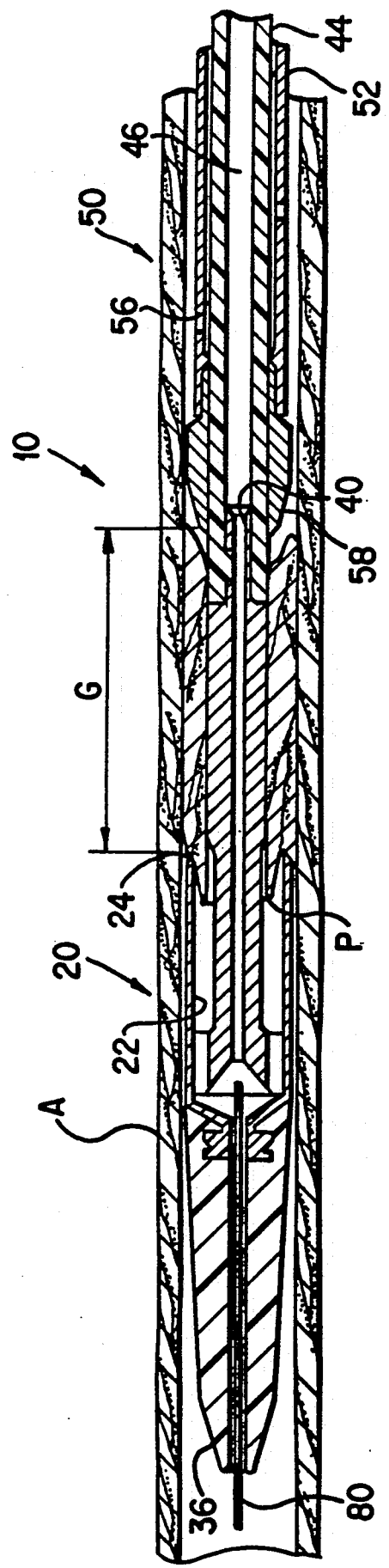
FIG. 5 is a cross section of the distal end of the ETEC in an open position showing cutting and collecting of stenotic plaque.

FIG. 5 shows the ETEC 10 with the distal end of the cut/collect catheter 20 advanced over a guide wire 80 beyond a stenotic plaque P within a human artery A. FIG. 5 shows the cutting edge 24 of the cylinder 22 being pulled back into the plaque P. During pullback, the cutting cylinder 22 could typically be rotated at approximately 2000 RPM while the closing catheter is not rotated. Thus, for most of the length of the ETEC 10 within the vessel, there is no rotating friction of any catheter outer surface against the vessel wall. This reduces the trauma to the vessel wall during the tissue excision procedure. The metal cannula 40 is somewhat longer than the gap G as shown in FIG. 5. Thus, even a curved vessel will tend to be straightened within the gap G. Thus, as the cutting edge 24 is being pulled back toward the metal tip 58, this vessel straightening effect will tend to reduce the probability of perforating the vessel wall during the excision procedure.

The cutting cylinder 22 is typically made from a hardened stainless cutlery steel such as Type 455. The remaining metal parts of ETEC 10 are typically made from a stainless steel such as Type 304 or 316. The plastic parts of the ETEC 10 are typically Nylon, or polyurethane or polyethylene, or other materials having similar properties.

The method for performing the tissue excision is as follows:

(1) The ETEC system with the cutting edge 24 held tight against the metal tip 58 and with the Touhy-Borst fitting 58 tightened would be advanced over a percutaneously inserted guide wire until the cutting edge 24 is advanced beyond the tissue to be excised.

(2) The fitting 58 is then loosened and the closing catheter 50 is pulled back until the full gap G (see FIG. 5) is realized, i.e., the proximal end 59 of the fitting 58 is in contact with the distal end 61 of the Luer fitting 60.

(3) The rotator 70 is advanced over the guide wire 80 and the Luer fitting 79 of the rotator 70 is attached to the Luer fitting 60 of the cut/collect catheter 20.

(4) The rotator gland 78 is then tightened around the guide wire 80.

(5) The rotator 70 is then turned on and simultaneously pulled back until the edge 24 is in contact with the metal tip 58.

(6) The rotator 70 is then promptly turned off; the gland 78 is loosened and then the fitting 79 of the rotator 70 is disconnected from the Luer fitting 60, and the rotator 70 is pulled off the guide wire 80.

(7) The gland 57 is then tightened and the ETEC 10 is pulled over the guide wire 80 and out of the living body.

(8) The gland 57 is then loosened, the closing catheter 50 is pulled back and a syringe (not shown) is then connected to the Luer fitting 60 while a finger is placed over the distal end of the flexible tip 36.

(9) Fluid is then firmly squirted into the lumen 46 of the cylinder 44 which forces the collected tissue to be pushed out of the tissue collection chamber 28. The tissue thus collected can then be histologically examined.

If there is a particularly long length of tissue to be excised from within the vessel, instead of merely pulling the cutting edge 24 back until it touches the stationary metal tip 58, the entire ETEC 10 can be pulled back while maintaining a fixed gap G between the cutting edge 24 and the metal tip 58. Once the desired length has been transversed by ETEC 10, then the metal tip 58 can be held fixed relative to the vessel while the cutting edge 24 is pulled back to it. This final closure provides containment of the cut tissue within the collection chamber 28.

Although most of the discussion herein concerns the excision of plaque from a human artery, the design of the ETEC system is such that it is well suited to excise tissue from a variety of vessels from within a living body, for example for the purpose of biopsy. In one such use, the ETEC system could be advanced over a guide wire into a bile duct and there it could be used to obtain a tissue sample for biopsy. Further, excision of tissue from the urethra, ureter, fallopian tubes or other vessels of a living body could be readily accomplished with the ETEC system.

Still further ETEC could be used to simultaneously remove thrombus and plaque in an early stage of myocardial infarction thus opening a clogged coronary artery for the free flow of blood. An anti-thrombogenic agent such as tPA could simultaneously be injected into the artery through the vent holes at the distal end of the closing catheter in order to efficiently dissolve any residual thrombus.

The ETEC system could also be used to remove plaque that has been dissected off the wall of an artery subsequent to balloon angioplasty. Such action could readily be used to open a clogged artery and preclude the necessity for vascular surgery.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A catheter system for the excision of obstructive tissue from within a vessel of a living body comprising:

a guide wire able to be advanced within a vessel in a living body such that the distal end of said guide wire is advanced beyond the obstructive tissue;

a cut/collect catheter having an interior lumen forming a passageway for said guide wire and which can be advanced over said guide wire until the distal end of said cut/collect catheter is situated beyond the tissue to be excised, said cut/collect catheter having a distal portion at which is located a single, concentric, hollow cylindrical cutting blade having a tissue collection chamber formed within its interior surface and said cutting blade having a cutting edge facing toward the proximal end of said cut/collect catheter for cutting obstructive tissue as said cut/collect catheter is pulled back in a retrograde direction; and, a closing catheter which surrounds the cut/collect catheter for most if its length, said closing catheter being adapted to move slidably along said cut/collect catheter and said closing catheter having a tapered distal portion which is tapered in the distal direction and adapted to make secure contact against the proximal end of said cylindrical cutting blade of said cut/collect catheter after the obstructive tissue has been cut so as to secure the cut tissue within said collection chamber.

2. The apparatus of claim 1 wherein a hollow flexible tip is joined at the distal end of said of said cut-collect catheter so as to better track over said guide wire.

3. The apparats of claim 2 wherein said hollow, flexible tip is made from an elastomer.

4. The apparatus of claim 1 wherein a passageway is formed between the interior lumen of said cut/collect catheter and said collection chamber which provides fluid communication between said interior lumen of said cut/collect catheter and said collection chamber for the purpose of flushing out tissue that has been collected in said collection chamber.

5. The apparats of claim 1 wherein the distal end of said closing catheter is fabricated from metal and shaped to prevent direct contact with said cutting edge of said cut/collect catheter so as to preclude dulling of said cutting edge.

6. The apparatus of claim 1 wherein the distal end of said closing catheter is fabricated from a plastic material so as to prevent dulling of said cutting edge of said cut/collect catheter when said closing catheter's distal end makes contact with said cutting edge.

7. The apparatus of claim 1 wherein vent holes are formed near the distal end of said closing catheter which are in fluid communication with the proximal end of said closing catheter lying outside the living body for the purpose of injecting fluids into the vessel at said closing catheter's distal end.

8. The apparatus of claim 7 wherein check valve means are provided at said closing catheter's proximal end to prevent the back flow of blood.

9. The apparatus of claim 7 wherein stop cock means are provided at said closing catheter's proximal end to prevent the back flow of blood.

10. The apparatus of claim 1 further comprising separation gap control means which limits the distance that said distal end of said closing catheter can be pulled back from said cutting edge of said cylindrical cutting blade.

11. A catheter system for the excision of obstructive tissue from within a vessel of a living body comprising:

a cut/collect catheter having a concentric cylindrical cutting blade at a distal portion and which can be advanced within said vessel of said living body until its distal end is situated beyond the tissue to be excised, said cylindrical cutting blade having at least one cutting edge facing toward the proximal end of said cut/collect catheter for cutting obstructive tissue as said cut/collect catheter is pulled back in a retrograde direction, and said cylindrical cutting blade having an interior surface shaped to form a tissue collection chamber for collecting the cut tissue;

a closing catheter which surrounds the cut/collect catheter for most if its length, said closing catheter having a tapered distal portion tapered in the distal direction and adapted to make secure contact against the proximal end of said cylindrical cutting blade of said cut/collect catheter after the obstructive tissue has been cut so as to secure the cut tissue within said collection chamber; and, a rotating means attached to the proximal end of said cut/collect catheter for the purpose of rotating said cylindrical cutting blade as it is pulled back through obstructive tissue within a vessel of a living body.

12. The apparatus of claim 11 wherein said rotating means emits an audio tone which is a function of its rotational speed.

13. The apparatus of claim 12 wherein said audio tone decreases in pitch when said cut/collect catheter encounters increased torque resistance.

14. The apparatus of claim 11 further comprising a guide wire means which can be advanced within said vessel in a living body such that the distal end of said guide wire is advanced beyond the obstructive tissue, and wherein said rotating means includes a passageway for said guide wire whereby said guide wire enters said rotating means at its distal end and emerges from said rotating means at its proximal end.

15. The apparatus of claim 14 wherein said rotating means includes a means to prevent rotation of said guide wire when said rotating means is rotating.

16. A method for removing obstructive tissue from a vessel of a living body comprising the steps of:

advancing a guide wire within a vessel in a living body until its distal end lies beyond the obstructive tissue;

advancing together a cut/collect catheter having an interior lumen forming a passageway for said guide wire and having at least one cutting edge located near its distal end and a closing catheter having a tapered distal end that is tapered in the distal direction over said guide wire until said cutting edge is situated beyond the tissue to be excised;

pulling back on said closing catheter so as to expose the at least one cutting edge located near the distal end of said cut/collect catheter;

pulling back on said cut/collect catheter so as to cut and collect the obstructive tissue; and removing the entire apparatus including the cut and collected obstructive tissue from the living body.

17. The method of claim 16, further comprising the steps of:

attaching a rotating means at the proximal end of said cut/collect catheter;

turning on the rotating means as the cut/collect catheter is pulled back through the obstructive tissue; and turning off the rotating means after said cutting edge makes contact with the distal end of said closing catheter.

18. The method of claim 17, further comprising the step of feeding said guide wire through said rotating means prior to turning on said rotating means.

19. The method of claim 18, further comprising the step of clamping down on said guide wire within said rotating means to prevent rotation of said guide wire when said rotating means is turned on.

20. The method of claim 16, further comprising the step of flushing out of the collected tissue after said cut/collect catheter has been removed from the living body.

21. The method of claim 16, further comprising the step of injecting a fluid from the proximal end of said closing catheter so that said fluid is vented from holes located near said closing catheter's distal end.

22. The method of claim 21 wherein said fluid is contrast medium for obtaining fluoroscopic visualization.

23. The method of claim 21 wherein said fluid is a medication.

24. The method of claim 16, further comprising the step of removing intimal tissue broken off the wall of an artery as a result of balloon angioplasty dilation of that artery.

25. The method of claim 16 wherein said tissue to be excised is both thrombus and plaque within an artery of a living body.

26. The method of claim 25 wherein said method is applied to the treatment of acute myocardial infarction.

27. The method of claim 16 wherein said vessel lies within the urogenital tract of said living body.

28. The method of claim 16 wherein said vessel lies within the digestive tract of said living body.

29. The method of claim 16 wherein said vessel is a bile duct.

* * * * *